(12) United States Patent
Yanni

(10) Patent No.: US 6,649,602 B1
(45) Date of Patent: Nov. 18, 2003

(54) USE OF AN H1 ANTAGONIST AND A SAFE STEROID TO TREAT EYE CONDITIONS

(75) Inventor: John M. Yanni, Burleson, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/069,851

(22) PCT Filed: Oct. 26, 2000

(86) PCT No.: PCT/US00/29436

§ 371 (c)(1),
(2), (4) Date: Feb. 28, 2002

(87) PCT Pub. No.: WO01/35963

PCT Pub. Date: Oct. 26, 2000

Related U.S. Application Data

(60) Provisional application No. 60/166,194, filed on Nov. 18, 1999.

(51) Int. Cl.⁷ ............................ A61K 31/56; A61K 31/50
(52) U.S. Cl. ........................ 514/169; 514/171; 514/253; 514/912
(58) Field of Search ................................. 514/253, 169, 514/171, 912

(56) References Cited

U.S. PATENT DOCUMENTS

| | | | |
|---|---|---|---|
| 5,149,694 A | 9/1992 | Cagle et al. | 514/40 |
| 5,192,780 A | 3/1993 | York et al. | 514/357 |
| 5,223,493 A | 6/1993 | Boltralik | 514/180 |
| 5,420,120 A | 5/1995 | Boltralik | 514/172 |
| 5,668,133 A | 9/1997 | Yanni et al. | 514/253 |

*Primary Examiner*—Zohreh Fay
(74) *Attorney, Agent, or Firm*—Teresa J. Schultz

(57) ABSTRACT

Composition and method of treating VKC, GPC, and AKC with H1 antagonists and ocularly safe steroids are disclosed.

9 Claims, No Drawings

USE OF AN H1 ANTAGONIST AND A SAFE STEROID TO TREAT EYE CONDITIONS

This application claims priority from PCT Application No. US00/29436, filed Oct. 26, 2000, which claims priority from U.S. No. 60/166,194, filed Nov. 18, 1999.

The present invention is directed to the use of an $H_1$ antagonist in combination with an ocularly safe steroid to treat ocular conditions, specifically vernal keratoconjunctivitis (VKC), giant papillary conjunctivitis (GPC), and atopic keratoconjunctivitis (AKC).

BACKGROUND OF THE INVENTION

Vernal keratoconjunctivitis (VKC), giant papillary conjunctivitis (GPC), and atopic keratoconjunctivitis (AKC) have historically been treated with a regimen of oral or topical antihistamines and/or oral or topical steroids with varying degrees of success (when used individually). Systemic treatment typically requires higher concentrations of the drug compound to be administered to afford an effective concentration to reach the necessary treatment site. Antihistamine compounds are known to have central nervous system (CNS) activity, which manifests itself in drowsiness and may have anticholinergic activity which manifests itself in the drying of mucus membranes. Steroid therapy also has significant systemic side effects, including the elevation of intraocular pressure (IOP). Topical ocular use of steroids can also cause a rise in IOP and induce cataract formation.

Topical ocular combination therapy is known. For example, U.S. Pat. No. 5,192,780 (York, et al) discloses the use of an antihistamine and an antiallergic for treating ophthalmic allergic responses. U.S. Pat. No. 5,149,694 (Cagle, et al.) discloses compositions of tobramycin and dexamethasbne for the control of infection and inflammatory response.

The use of an $H_1$ antagonist in combination with a safe steroid for treating VKC, GPC, and AKC is not known.

SUMMARY OF THE INVENTION

The present invention is directed to compositions of combinations of $H_1$ antagonists and safe steroids to treat VKC, GPC, and AKC. Methods for the use of the compositions in mammals are also contemplated.

DESCRIPTION OF PREFERRED EMBODIMENTS

The current invention comprises compositions of $H_1$ antagonists for treating the itching, redness, and edema associated with VKC, GPC, and AKC. The compositions also include a safe steroid, as used herein the term "safe steroid" means a steroid which treats eosinophil and neurotrophil associated inflammation, reduces papillae formation, and which is effective in treating inflammation without causing a clinically significant elevation in IOP.

The $H_1$ antagonists which are useful according to the present invention include all efficacious compounds, including, but not limited to: emedastine, levocabastine, mequitazine, chlorpheniramine, brompheniramine, astemizole, cetirizine, terfenadine, rocastine, loratadine, 5-[2-[4-bis(4-fluorophenyl)hydroxymethyl-1-piperidinyl] ethyl]-3-methyl]-2-oxazolidinone ethanedioate) pyrilamine, clemastine, azelastine, ketotifen, olopatadine, and mapinastine.

Safe steroids which can be used herein include any glucocorticoid which meets the safe steroid definition, including but not limited to, fluoromethalone, rimexolone, loteprednol, dexamethasone beloxil and its analogues described in U.S. Pat. Nos. 5,223,493 and 5,420,120.

The $H_1$ antagonists and safe steroids (compounds) can be incorporated into various types of ophthalmic formulations for delivery to the eye. These compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solution may also contain a thickener such as hydroxymethylcellulose, hydroxyethylcellulose, hydroxypropylmethylcellulose, methylcellulose, polyvinylpyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

The compounds are preferably formulated as topical ophthalmic suspensions or solutions, with a pH of about 6.0 to 8.0. The $H_1$ antagonists will normally be contained in these formulations in an amount 0.01% to 0.3% by weight, but preferably in an amount of 0.05% to 0.1% by weight. The safe steroids will normally be contained in those formulations in an amount 0.05% to 1.5% by weight, but preferably in an amount of 0.1% to 1.0% by weight. Thus, for topical presentation 1 to 2 drops of these formulations would be delivered to the surface of the eye up to 4 times per day according to the routine discretion of a skilled clinician.

The preferred compositions of the present invention includes 0.01% to 0.05% emedastine and 0.1% to 1.0% dexamethasone beloxil or loteprednol.

The following example is illustrative of the composition of the present invention, but in no way limiting.

EXAMPLE

| Ingredient | Weight % |
| --- | --- |
| Emedastine | 0.05% |
| Dexamethasone beloxil | 0.1% |
| Hydroxypropyl methylcellulose | 0.5% |
| Dibasic sodium phosphate | 0.2% |
| Disodium EDTA | 0.01% |
| Sodium Chloride | 0.75% |
| Polysorbate 80 | 0.01% |
| Benzalkonium chloride | 0.01% |
| Sodium hydroxide, hydrochlorine acid | adjust to approx. 7.0 |
| Water | q.s. 100% |

I claim:

1. A method of treating ocular conditions in mammals selected from the group consisting of vernal keratoconjunctivitis, giant papillary conjunctivitis, and atopic keratoconjunctivitis which comprises administering a pharmaceutically effective amount of a composition comprising an $H_1$ antagonist and a safe steroid.

2. The method of claim 1 wherein the $H_1$ antagonist is selected from the group consisting of emedastine, levocabastine, mequitazine, chlorpheniramine, brompheniramine, astemizole, cetirizine, terfenadine, rocastine, loratadine, 5-[2-[4-bis (4-fluorophenyl) hydroxymethyl-1-piperidinyl]ethyl]-3-methyl]-2-oxazolidinone ethanedioate) pyrilamine, clemastine, azelastine, ketotifen, olopatadine, and mapinastine.

3. The method of claim 2 wherein the $H_1$ antagonist is emedastine.

4. The method of claim 1 wherein the safe steroid is selected from the group consisting of fluoromethalone, rimexolone, loteprednol, dexamethasone beloxil.

5. The method of claim 4 wherein the safe steroid is selected from the group consisting of dexamethasone beloxil and loteprednol.

6. The method of claim 1 wherein the $H_1$ antagonist is emedastine and the safe steroid is dexamethasone beloxil.

7. The method of claim 1 wherein the $H_1$ antagonist is emedastine and the safe steroid is loteprednol.

8. The method of claim 1 wherein the $H_1$ antagonist is olopatadine.

9. The method of claim 8 wherein the safe steroid is dexamethasone beloxil or loteprednol.

* * * * *

UNITED STATES PATENT AND TRADEMARK OFFICE
CERTIFICATE OF CORRECTION

PATENT NO. : 6,649,602 B1
DATED : November 18, 2003
INVENTOR(S) : John M. Yanni

It is certified that error appears in the above-identified patent and that said Letters Patent is hereby corrected as shown below:

Column 1,
Lines 62-64, "5-[2-[4-bis(4-fluorophenyl)hydroxymethyl-1-piperidinyl]ethyl]-3-methyl]-2-oxazolidinone ethanedioate) pyrilamine" should read -- 5-[2-[4-bis(4-fluorophenyl)hydroxymethyl-1-piperidinyl]ethyl]-3-methyl-2-oxazolidinone ethanedioate, pyrilamine, --

Column 3,
Lines 5-7, "5-[2-[4-bis(4-fluorophenyl)hydroxymethyl-1-piperidinyl]ethyl]-3-methyl]-2-oxazolidinone ethanedioate) pyrilamine" should read -- 5-[2-[4-bis(4-fluorophenyl)hydroxymethyl-1-piperidinyl]ethyl]-3-methyl-2-oxazolidinone ethanedioate, pyrilamine, --

Signed and Sealed this

First Day of June, 2004

JON W. DUDAS
*Acting Director of the United States Patent and Trademark Office*